US00PP34796P3

(12) United States Plant Patent
Brown

(10) Patent No.: US PP34,796 P3
(45) Date of Patent: Dec. 6, 2022

(54) ***CALLISTEMON* PLANT NAMED 'CNU19'**

(50) Latin Name: *Callistemon citrinus*
Varietal Denomination: 'CNU19'

(71) Applicant: Nuflora International Pty Ltd, Macquarie Fields (AU)

(72) Inventor: Graham Brown, Bowral (AU)

(73) Assignee: Nuflora International Pty Ltd, Macquarie Fields (AU)

( * ) Notice: Subject to any disclaimer, the term of this patent is extended or adjusted under 35 U.S.C. 154(b) by 0 days.

(21) Appl. No.: 17/803,223

(22) Filed: Mar. 21, 2022

(65) Prior Publication Data

US 2022/0304204 P1 Sep. 22, 2022

Related U.S. Application Data

(60) Provisional application No. 63/163,816, filed on Mar. 20, 2021.

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ..... A01H 5/02; A01H 5/00
See application file for complete search history.

(56) References Cited

PUBLICATIONS https://australianplantspecialists.com.au/wp-content/uploads/2021/05/Full-range-2020.21.pdf; May 2021; pp. 1-12.*

* cited by examiner

*Primary Examiner* — Kent L Bell
(74) *Attorney, Agent, or Firm* — Samuel R. McCoy, Jr.

(57) ABSTRACT

A new and distinct variety of *Callistemon* plant named 'CNU19' which is characterized by the combination of a semi-compact, globular growth habit, an abundance of cylindrical inflorescences bearing dark pink flowers, and the stability of all characteristics from generation to generation.

2 Drawing Sheets

Latin name of the genus and species: The Latin name of the genus and species of the novel variety disclosed herein is *Callistemon citrinus.*

Variety denomination: The inventive variety of *Callistemon* disclosed herein has been given the variety denomination 'CNU19'.

BACKGROUND OF THE INVENTION

Parentage: 'CNU19' is the result of a controlled cross-pollination breeding program carried out by the inventor at a commercial plant breeding facility in Cobbitty, New South Wales, Australia in October of 2014. The inventor performed a controlled cross-pollination of the seed parent, *Callistemon* 'Hot Pink' (South African Plant Breeder's Rights grant number ZA 20043189) with *Callistemon* 'Mauve Mist' (unpatented), the pollen parent. The resulting seedlings were grown for two years to evaluate for new and distinct characteristics. In October of 2016, the inventor selected the new *Callistemon* plant for its upright growth habit and dark pink flowers. This new and distinctive cultivar was given the name 'CNU19'

Asexual Reproduction: Asexual reproduction of 'CNU19', by way of stem cuttings, was first initiated in 2016 in Cobbitty, New South Wales, Australia. Through greater than four subsequent generations of asexual propagation, the unique features of this cultivar have proven to be stable and true to type.

SUMMARY OF THE INVENTION

The cultivar 'CNU19' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'CNU19'. These characteristics in combination distinguish 'CNU19' as a new and distinct *Callistemon* cultivar:

1. *Callistemon* 'CNU19' exhibits a semi-compact, globular growth habit; and
2. *Callistemon* 'CNU19' exhibits an abundance of cylindrical inflorescences bearing dark pink flowers; and
3. *Callistemon* 'CNU19' exhibits flowers with dark pink exserted stamens.

BOTANICAL DESCRIPTION OF THE PLANT

Figure 1:
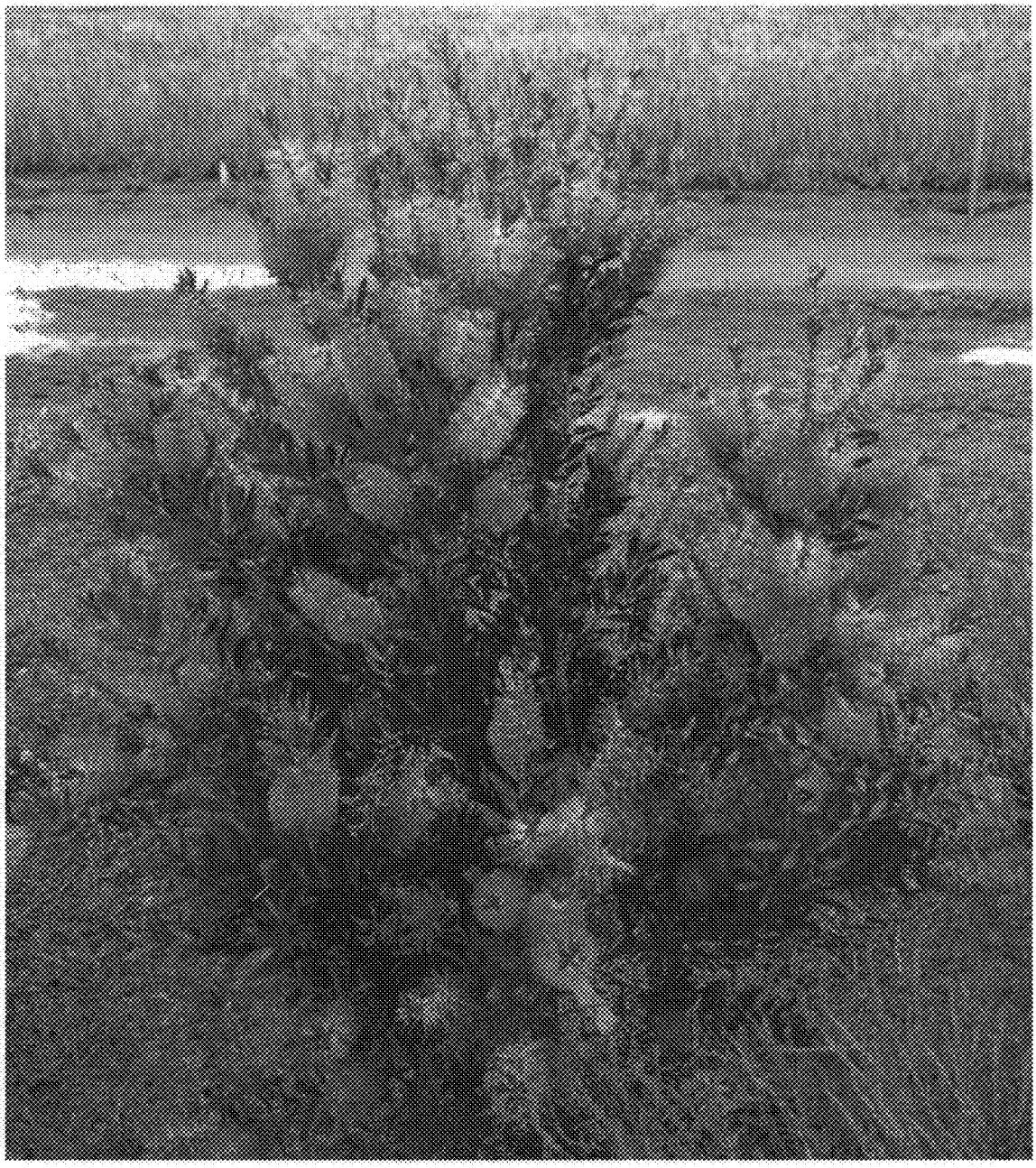
FIG. 1 illustrates, as nearly true as it is reasonably possible to make the same in color photographs of this type, an exemplary plant of 'CNU19'. This plant is approximately 36 months old.
Figure 2:
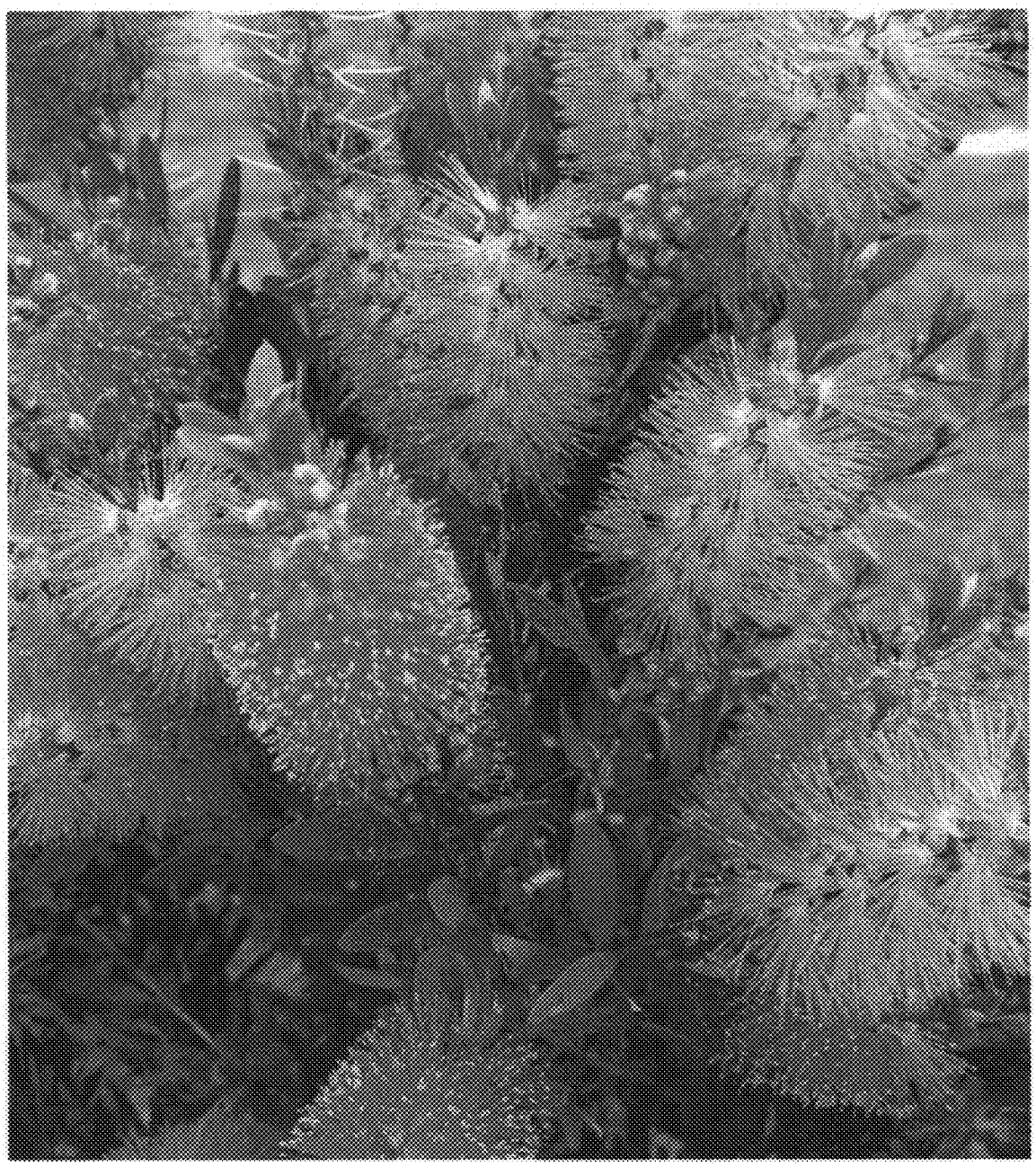
FIG. 2 illustrates, as nearly true as it is reasonably possible to make the same in color photographs of this type, the typical inflorescence of 'CNU19'.

The following observations and measurements were made in May of 2022 and describe a 6-year-old 'CNU19' plant grown in the ground in Clarendon, New South Wales, Australia. The plant was allowed to grow with full sun exposure and maintained with sporadic overhead irrigation during prolonged drought conditions and slow-release granular fertilizer applications. The plant received a light prune, biannually. No pest or disease control measures were utilized in production.

Those skilled in the art will appreciate that certain characteristics will vary with older or, conversely, with younger plants. 'CNU19' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 (third edition).

A botanical description of 'CNU19', comparisons with the parents, comparisons with sibling cultivars, and a comparison with the most similar variety of common knowledge are provided below.

General plant description:

*Growth habit.*—Evergreen shrub with a semi-compact, globular growth habit.

*Plant profile.*—Rotund.

*Height.*—140 cm from the soil level to the top of the foliar plane.

*Plant spread.*—130 cm.

*Growth rate.*—Moderately fast.

*Plant vigor.*—Moderately vigorous.

*Propagation type.*—Stem cuttings.

*Time to produce a rooted cutting.*—Approximately 120 days to produce a rooted cutting at approximately 25 degrees Celsius.

*Time to produce a finished plant.*—32 weeks to produce a fully rooted 15 cm container.

*Disease and pest resistance.*—Neither resistance nor susceptibility to typical *Callistemon* pests and diseases has been observed.

*Environmental tolerances.*—Adapt to, at least, USDA Zones 9 through 11; moderate tolerance to rain; moderate to high tolerance to wind; drought tolerant once established.

Root system:

*General.*—Moderately dense and freely branched rooting; roots are moderately fibrous.

*Distribution in the soil profile.*—Shallow to moderately deep.

Stem:

*General branching habit.*—A single main stem, freely branching from the base, with an abundance of lateral branches.

*Quantity of main stems per plant.*—1.

*Diameter of the main stem.*—8.0 cm at soil level.

*Abundance of lateral branches.*—Abundant.

*Length of lateral branches.*—Approximately 83 cm.

*Diameter of lateral branches.*—Approximately 1.1 cm.

*Internode length.*—Ranging from 0.3 cm to 0.45 cm.

*Attitude of lateral branches.*—Outward to upright.

*Aspect.*—Rounded.

*Texture, juvenile.*—Tomentose.

*Texture, mature and oldest wood.*—Glabrous and becoming progressively fissured and furrowed with age, followed by exfoliation of the outer bark in small segments, revealing yet more fissured and furrowed bark beneath.

*Luster.*—Slightly glossy to matte.

*Strength.*—Strong.

*Color, juvenile lateral branches.*—Greyed-purple, nearest to in between RHS 181B and 181C; as stems mature, they become progressively suffused with greyed-orange, nearest to in between RHS 172C and 172D.

*Color, mature lateral branches.*—Greyed-orange, distally, nearest to RHS 167D, and transitioning to greyed-white near the proximal end of the stem, RHS 196B.

*Color, main stem and oldest wood of lateral branches.*—Exfoliating bark is a combination of greyed-green and brown, nearest to RHS 196A, 200A, 200B, and 200D; exposed wood below the exfoliating bark is greyed-orange, nearest to a combination of RHS 164A, 164C, 164D, and 166C.

Foliage:

*Arrangement.*—Whorled.

*Division.*—Simple.

*Attachment.*—Petiolate.

*Attitude.*—Upward and outward.

*Lamina.*—Shape — Narrowly lanceolate. Aspect — Flat. Dimensions — 7.0 cm long and 1.3 cm wide. Apex — Broad acute with a very short, soft mucronate tip. Base — Cuneate. Margin — Entire; not undulated. Texture of the juvenile foliage, adaxial surface — Tomentose. Texture of the juvenile foliage, abaxial surface — Tomentose. Texture of the mature foliage, adaxial surface — Coriaceous; glabrous. Texture of the mature foliage, abaxial surface — Coriaceous; glabrous. Luster of the juvenile foliage, adaxial surface — Matte. Luster of the juvenile foliage, abaxial surface — Matte. Texture of the mature foliage, adaxial surface — Slightly glossy. Texture of the mature foliage, abaxial surface — Matte to slightly glossy. Color — Juvenile foliage, adaxial surface — Greyed-purple, nearest to in between RHS 183D and 184B. Lamina becomes progressively suffused with green, RHS 137C, with age. Juvenile foliage, abaxial surface — Greyed-purple, nearest to in between RHS 184B and 184C. Lamina becomes progressively suffused with green, RHS 137C, with age. Mature foliage, adaxial surface — Nearest to in between green and yellow-green, RHS 137A and 147A. Mature foliage, abaxial surface — Green, nearest to in between RHS 137B and 137C. Venation — Pattern — Pinnate. Color, adaxial surface — Same as the surrounding foliage; nearest to in between green and yellow-green, RHS 137A and 147A. Color, adaxial surface — Same as the surrounding foliage; green, nearest to in between RHS 1378 and 137C.

*Petiole.*—Length — 0.15 cm. Diameter — 0.15 cm at the base. Strength — Strong. Texture, juvenile — Tomentose. Texture, mature — Smooth; glabrous. Luster, juvenile — Matte. Luster, mature — Slightly glossy. Color, adaxial and abaxial surfaces — Juvenile petioles are greyed-purple, nearest to RHS 183D, and suffused with yellow-green near the base, RHS 151B. Mature petioles are yellow-green, nearest to RHS 151A.

*Stipules.*—None observed.

Inflorescence:

*Habit*.—Terminal leafy spikes, borne directly on the lateral branches.

*Natural flowering season*.—Heaviest bloom period is spring, with sporadic flowering through summer and a second larger flush of blooms in autumn, in Zone 9 of the United States.

*Time to flower or response time*.—Approximately 6 months.

*Dimensions*.—Largest inflorescence observed is 7.1 cm long and 6.2 cm in diameter.

*Quantity of flowers per inflorescence*.—Ranging from approximately 30 to as many as 40 flowers.

*Peduncles*.—None.

Flower buds:

*Shape*.—Broad oblong to obovoid.

*Length*.—7.0 mm.

*Diameter*.—3.5 mm.

*Texture*.—Coriaceous; proximal end at the calyx tube is tomentose and distal end at the flower petals is glabrous.

*Luster*.—Slightly glossy.

*Color*.— Yellow-green, nearest to RHS 145A, and fading lighter towards the apex, nearest to RHS 145C; immature sepal lobes are suffused with red-purple, nearest to RHS 61B.

Flower:

*Shape, type*.—Rotate, with a single whorl of petals.

*Attachment*.—Sessile.

*Flowering habit*.—Freely flowering.

*Attitude*.—Upright to outward.

*Flower longevity on plant*.—Approximately 7 to 10 days.

*Persistent or self-cleaning*.—Self-cleaning.

*Fragrance*.—Non-fragrant.

*Diameter*.—Diameter of the corolla is 7.5 mm; the width across the exserted stamens at their distal end is 24.0 mm.

*Depth*.—Depth of the corolla, including the exserted stamens, is 23.5 mm.

*Pedicels*.—None; flowers are sessile.

*Calyx*.—Shape — Campanulate with sepal lobes adpressed to the corolla at anthesis. Length — 4.5 mm, including the sepal lobes. Diameter — 3.5 mm, distally, at the sepal lobes. Color of the calyx tube — Yellow-green, nearest to in between RHS 144C and 144D. Sepal lobes — Quantity — 5. Shape — Deltoid. Dimensions — 1.0 mm long and 1.9 mm wide at the base. Apex — Obtuse. Base — Fused to the calyx tube. Margin — Entire. Texture — Tomentose. Luster — Matte. Color — Yellow-green, nearest to in between RHS 144C and 144D, and suffused with red-purple, nearest to RHS 61B.

*Petals*.—Quantity — 5. Arrangement — Rotate. Length — 3.25 mm. Width — 3.0 mm. Shape — Near orbicular. Apex — Obtuse. Base — Truncate. Margin — Entire; light undulation. Texture, inner surface — Glabrous; coriaceous. Texture, outer surface — Glabrous; coriaceous. Petal color — When opening, inner surface — Yellow-green, nearest to RHS 154D. When opening, outer surface — Yellow-green, nearest to RHS 154D. Fully opened, inner surface — Yellow-green, nearest to RHS 154D. Fully opened, lower surface — Yellow-green, nearest to RHS 154D. Petal venation color — No venation is visible.

Reproductive organs:

*Androecium*.—Stamens — Quantity — 34, on average. Anthers — Attachment — Dorsifixed. Shape — Oblong. Dimensions — 0.75 mm long and 0.5 mm wide. Color — Greyed-yellow, nearest to a combination of RHS 160B and 161B, with pollen removed. Filaments — Length — 16.25 mm, on average. Diameter — 0.5 mm. Color — Red-purple, nearest to in between RHS 66A and 67A. Amount of Pollen — Abundant. Pollen color — Yellow, nearest to RHS 1C.

*Gynoecium*.—Pistil — Quantity — One. Length — 17.5 mm. Style — Length — 16.75 mm, on average. Diameter — 0.5 mm at the base. Color — Red-purple, nearest to RHS 67B, and fading lighter towards the base, nearest to RHS 67D. Stigma — Shape — Near globular. Length — 0.75 mm. Diameter — 0.5 cm. Color — Greyed-yellow, RHS 161D, and suffused with yellow-green, RHS 153D. Ovary position — Inferior.

Seed and fruit: Seeds not observed.

COMPARISONS WITH THE PARENT PLANTS

Plants of the new cultivar 'CNU19' differ from its seed parent, *Callistemon* 'Hot Pink' (South African Plant Breeder's Rights grant number ZA 20043189), by the characteristics described in Table 1.

TABLE 1

| Characteristic | 'CNU19' | 'Hot Pink' |
|---|---|---|
| General coloration of the stamens. | Dark pink. | Red-purple. |

Plants of the new cultivar 'CNU19' may be distinguished from its pollen parent, *Callistemon* 'Mauve Mist' (not patented), by the characteristics described in Table 2.

TABLE 2

| Characteristic | 'CNU19' | 'Mauve Mist' |
|---|---|---|
| General coloration of the stamens. | Dark Pink. | Purple. |

COMPARISON WITH THE MOST SIMILAR VARIETIES OF COMMON KNOWLEDGE

Plants of the new cultivar 'CNU19' may be distinguished from the most similar known comparator, *Callistemon* 'CNU06' (co-pending U.S. Plant patent application Ser. No. 17/803,228), by the characteristics described in Table 3.

TABLE 3

| Characteristic | 'CNU19' | 'CNU06' |
|---|---|---|
| Growth habit. | More upright. | More spreading. |
| Plant height. | Typically taller than 'CNU06'. | Typically shorter than 'CNU19'. |

TABLE 3-continued

| Characteristic | 'CNU19' | 'CNU06' |
|---|---|---|
| Plant width. | Typically narrower than 'CNU06'. | Typically broader than 'CNU19'. |
| General coloration of the stamens. | Dark pink, yet generally appearing as a brighter shade of pink relative to 'CNU06'. | Dark pink, yet generally appearing as a darker shade of pink relative to 'CNU06'. |

Plants of the new cultivar 'CNU19' may be distinguished from its sibling, *Callistemon citrinus* 'CNU01' (co-pending U.S. Plant patent application Ser. No. 17/803,225), by the characteristics described in Table 4.

TABLE 4

| Characteristic | 'CNU19' | 'CNU01' |
|---|---|---|
| Growth habit. | Semi-compact; globular. | Compact; globular to near columnar. |
| Plant height. | Typically taller than 'CNU01'. | Typically shorter than 'CNU19' |
| General coloration of the stamens. | Dark Pink. | White. |

Plants of the new cultivar 'CNU19' may be distinguished from its sibling, *Callistemon citrinus* 'CNU07' (co-pending U.S. Plant patent application Ser. No. 17/803,227), by the characteristics described in Table 5.

TABLE 5

| Characteristic | 'CNU19' | 'CNU07' |
|---|---|---|
| Growth habit. | Semi-compact; globular. | Compact; globular. |
| Plant height. | Taller than 'CNU07'. | Shorter than 'CNU19' |
| General coloration of the stamens. | Dark Pink. | White. |

Plants of the new cultivar 'CNU19' may be distinguished from its sibling, *Callistemon citrinus* 'CNU15' (co-pending U.S. Plant patent application Ser. No. 17/803,224), by the characteristics described in Table 6.

TABLE 6

| Characteristic | 'CNU19' | 'CNU15' |
|---|---|---|
| Plant size. | Larger than 'CNU15'. | Smaller than 'CNU06' |
| Foliage size. | Larger than 'CNU15'. | Smaller than 'CNU06' |
| Inflorescence size. | Larger than 'CNU15'. | Smaller than 'CNU06' |
| General coloration of the stamens. | Dark Pink. | Light Pink. |

That which is claimed is:

1. A new and distinct variety of *Callistemon* plant named 'CNU19', substantially as described and illustrated herein.

* * * * *